United States Patent [19]

Eitenmuller et al.

[11] Patent Number: 4,610,692
[45] Date of Patent: Sep. 9, 1986

[54] IMPLANT FOR FILLING BONE CAVITIES AND FIXING BONE FRAGMENTS IN A LIVING BODY, METHOD OF PRODUCING THE SAME, AND BONE IMPLANT SYSTEM

[75] Inventors: Jürgen Eitenmuller, Brauweiler; Helmut Rackur, Remchingen/Singen; Walter Wimmer; Marija Weiss, both of Limburg/Lahn, all of Fed. Rep. of Germany

[73] Assignee: Mundipharma GmbH, Fed. Rep. of Germany

[21] Appl. No.: 623,364

[22] Filed: Jun. 22, 1984

Related U.S. Application Data

[63] Continuation-in-part of Ser. No. 350,341, Feb. 19, 1982, abandoned.

[30] Foreign Application Priority Data

| Feb. 20, 1981 | [DE] | Fed. Rep. of Germany | 3106445 |
| Jul. 3, 1981 | [DE] | Fed. Rep. of Germany | 3126273 |
| Aug. 20, 1981 | [DE] | Fed. Rep. of Germany | 3133015 |
| Aug. 20, 1981 | [DE] | Fed. Rep. of Germany | 3133016 |

[51] Int. Cl.$^4$ .................................. A01N 25/26
[52] U.S. Cl. ............................... 623/16; 128/92 C; 264/44; 264/60; 424/19; 424/80; 424/150; 604/890; 604/891; 623/66
[58] Field of Search ............... 604/890, 891; 3/1.9, 3/1.91, 1; 128/92 G, 92 C; 264/44, 60; 424/19, 80, 150; 623/16, 66

[56] References Cited

U.S. PATENT DOCUMENTS

| 4,322,398 | 3/1982 | Reiner et al. | 424/19 |
| 4,330,891 | 5/1982 | Branemark et al. | 3/1 |
| 4,347,234 | 8/1982 | Wahlig et al. | 424/19 |
| 4,371,484 | 2/1983 | Inukai et al. | 264/44 |
| 4,401,651 | 8/1983 | Knutson | 424/150 |
| 4,449,981 | 5/1984 | Drake et al. | 604/890 |
| 4,497,075 | 2/1985 | Niwa et al. | 623/16 |

FOREIGN PATENT DOCUMENTS

| 0058867 | 9/1982 | European Pat. Off. | 3/1.9 |
| 2620891 | 11/1977 | Fed. Rep. of Germany | 3/1.9 |
| 2485504 | 12/1981 | France | 3/1.9 |

OTHER PUBLICATIONS

Eitenmuller, J. et al. "Experimental and Preliminary Clinical Experience with Absorbable Calcium Phosphate Granules Containing an Antibiotic or Antiseptic for the Local Treatment of Osteomyelitis" Journal of Hospital Infection (1985)(Supplement), pp. 177–184.

The Merck Index–9th Ed., 1976, pp. 996–997, Items 7498 and 7499.

*Primary Examiner*—Helen M. McCarthy
*Attorney, Agent, or Firm*—Steinberg & Raskin

[57] ABSTRACT

A sintered tricalcium phosphate implant for filling bone cavities and for fixing bone fragments is provided, which comprises a discretely-shaped, porous body, at least one therapeutically-active ingredient impregnated into this porous body and distributed among the pores therein, and at least one coating of predetermined thickness of a biodegradable substance on at least a portion of this porous body, so that the time of absorption of the therapeutically-active ingredient is controlled by the thickness of the biodegradable substance. A process for producing this sintered tricalcium phosphate implant is also provided, along with an implant system for filling bone cavities and for fixing bone fragments in a living body, comprising a number of such tricalcium phosphate bone implants, with discrete coatings of biodegradable substance of predetermined thicknesses over at least some of the porous bodies constituting the tricalcium phosphate bone implants.

33 Claims, No Drawings

IMPLANT FOR FILLING BONE CAVITIES AND FIXING BONE FRAGMENTS IN A LIVING BODY, METHOD OF PRODUCING THE SAME, AND BONE IMPLANT SYSTEM

The present application is a continuation-in-part of U.S. Pat. application Ser. No. 350,341, filed Feb. 19, 1982, now abandoned.

BACKGROUND OF THE INVENTION

The present invention relates to a sintered tricalcium phosphate implant for filling bone cavities and for fixing bone fragments in a living body, and to a process for producing such a sintered, tricalcium phosphate implant. The present invention is also directed to an implant system for filling bone cavities and for fixing bone fragments within a living body.

Various compositions for implantation within bone are known, such compositions being used, e.g., for filling cavities within bone in a living body, affixing or cementing implants already disposed within a cavity of bone to the bone in a living body, anchoring joint endoprotheses, or for similar implantation purposes. Such bone implant compositions or cements may be inserted into the living body in the form of a plastic paste, which subsequently hardens due to polymerization in situ. Such a paste may be prepared by mixing primary polymers such as powdery methyl methacrylate homopolymers or copolymers, with suitable liquid monomers such as methyl methacrylate, along with a catalyst system, and, if necessary, radiopaque media for identifying the cement within the living body. Hardening naturally occurs due to polymerization of the monomer.

German Pat. Appl. DE-A No. 22 29 702 discloses a bone cement of polymethyl methacrylate and a monomer compound of methyl methacrylate and methacrylic acid esters of higher alcohols, along with a catalyst system of benzoyl peroxide and dimethyl-p-toluidine.

The inclusion of antibiotics in such bone implantation compositions or cements, for the purpose of preventing infection along the boundary surface between the cement and the bone within the living body, is also known. For example, Bild der Wissenschaft, 10, (1979) 114–126 discloses bone implants made of tricalcium ceramic material, used as a bone substitute, combined with antibiotics as a medicine depot at the fracture surface. According to DE-A No. 20 22 117, antibiotics which may be included in a bone implant composition or cement include penicillin, gentamycin and tetracycline. The antibiotic is initially released from the hardened bone cement at a relatively high concentration, thus obtaining the requisite bactericidal or bacteriostatic effect. However, a subsequent drop in antibiotic concentration within the bone implant or cement results in a lower release rate of antibiotic, this rate remaining constant over a longer period of time. Thus even though certain long-term or depot action is attained, the effective antibiotic concentration remains too low.

DE-B No. 25 11 122 discloses discloses an initial product for preparation of bone cement or implant material, which in addition to a gentamycin compound, contains either pulverulent copolymers of methyl methacrylate or monomeric methyl methacrylate as the principle constituent, as well as gentamycin hydrochloride and/or gentamycin hydrobromide, or a mixture of gentamycin sulfate with sodium chloride, potassium chloride, sodium bromide and/or potassium bromide. The resulting initial product for the preparation of bone cement releases the antibiotic at increased concentration than in the previously-noted products. However, the effectiveness of the antibiotic is not maintained over a long period of time.

EP-A-1 No. 0 003 979 (U.S. Pat. No. 4,322,398) describes an implantable pharmaceutical depot and a process for the production thereof. The base of this known implant is formed by a calcium phosphate matrix which is impregnated with a therapeutically-active component, and which also contains an auxiliary agent for generating the depot effect. Two possible variations for this combination of matrix, active component, and auxiliary agent are disclosed.

According to the first possible variation disclosed in EP-A-1 No. 0 003 979, the therapeutically active component is encapsulated with a polymer and subsequently inserted into the matrix. The encapsulated therapeutically-active component is is thus absorbed into the pores of the sintered matrix. However, the available volume (i.e. the volume within these pores) is thus partially filled by the polymer encapsulating the therapeutically active component, so that this volume is lost for the absorption of the active component itself. If the depot effect is set at a different timing by increasing the volume of the encapsulating polymer, then the available concentration of the active component is impaired to a greater or lesser degree.

According to the second possible variation disclosed in EP-A-1-0 003 979, instead of inserting the encapsulated active component into the finished matrix, the pulverized mixing components forming the matrix material along with the therapeutically active component, are all coated (i.e. all components forming the depot are coated at once). However, this is not suitable for producing a sintered molded implant, since the therapeutically active component and the auxiliary agent would both be destroyed by the heating required for the subsequent sintering process. Instead, a solid material is created by this second variation which is merely held together by the auxiliary agent, does not have the requisite strength for bone implantation, and where the calcium phosphate powder forming the matrix will not offer a supporting surface for the osteoblasts, which is essential for addition to, or implantation in bone within a living body.

Philips Technishe Rundschau Vol. 37 No. 9/10 (1977/78) 225–257, in explaining the suitability of calcium phosphate for implantation purposes, describes the possibility of producing specific porosities while sintering the bone implant. In order to exclusively generate small pores within the sintered implant apart from large pores therein, a specific quantity of hydrogen peroxide is added to the calcium phosphate prior to sintering, according to this reference. This chosen quantity of hydrogen peroxide, along with the heating rate of sintering, influence the macroporosity that occurs within the sintered article, while the microporosity occurring therein is influenced by other parameters.

DE-AL No. 27 25 665 (U.S. Pat. No. 4,230,455) discloses a baked and molded article formed of hydroxyapatite which has a fibrous insertion surrounded by hydroxyapatite with an additive, such as $AlF_3$. However, it is not disclosed in this reference whether there is any controllable depot affect of an active component. DE-AL No. 27 56 256 discloses a gel-type auxiliary agent for coating and/or filling bone defects, which contains at least one polysaccharide and which serves to create a sterile seal between the surface of a wound and the implant during the healing process.

Thus there are several drawbacks and disadvantages in the prior art concerning implantation within bone in a living body, notably with the effective, controlled release of a therapeutically active ingredient during the subsequent bone formation or healing process over a period of time.

SUMMARY OF THE INVENTION

Accordingly, it is an object of the present invention to improve formation and/or healing of bone within a living body.

It is also an object of the present invention to provide for therapeutic activation and/or supplementation of the formation and/or healing of bone within a living body.

It is another object of the present invention to provide for improved, controlled release/administration of therapeutically-active ingredient to bone as it is forming and/or healing within a living body.

It is a further object of the present invention to provide for sustained release/administration of therapeutically active ingredient to bone as it is forming and/or healing within a living body.

It is a further object of the present invention to provide for improved formation and/or healing of bone by concentrating release/administration of therapeutically-active ingredient at particular locations, such as highly damaged bone tissue or at locations extremely susceptible to infection.

These and other objects are attained by the present invention which provides a sintered tricalcium phosphate implant for filling bone cavities and for fixing bone fragments in a living body, comprising a discretely shaped, porous body of tricalcium phosphate, at least one therapeutically-active ingredient impregnated into said porous body and distributed among the pores therein, and at least one coating of predetermined thickness of a biodegradable substance on at least a portion of the porous body impregnated with therapeutically-active ingredient, whereby the time of absorption of said therapeutically-active ingredient is controlled by the thickness of said biodegradable substance.

The present invention also provides for a method of producing such sintered tricalcium phosphate implant, which comprises the steps of mixing tricalcium phosphate with at least one substance which under heat sufficiently high to bake said tricalcium phosphate, forms a gas, shaping the thus-formed mixture into shaped bodies thereof, baking the shaped bodies at a temperature sufficiently high to cause gas formation from said substance, thereby forming pores in said shaped bodies, impregnating said shaped porous bodies with a therapeutically active ingredient, thereby distributing the same in the pores, and coating at least a portion of one of said shaped, porous bodies having said therapeutically active ingredient distributed therein, with a coating of a predetermined thickness of a biodegradable substance, whereby the time of absorption of said therapeutically active ingredient is controlled by the thickness of said biodegradable substance.

The present invention is also directed to an implant system for filling bone cavities and for fixing bone fragments in a living body, comprising discretely shaped, porous bodies of tricalcium phosphate, at least one therapeutically-active ingredient impregnated into said porous bodies and distributed among the pores therein, and at least one coating of predetermined thickness of a biodegradable substance on at least a portion of one of the porous bodies impregnated with therapeutically-active ingredient, whereby the time of absorption of said therapeutically-active ingredient is controlled by the thickness of said biodegradable substance.

The present invention enables the release of therapeutically-active ingredient to be precisely controlled over time, to provide effective release of the therapeutically-active concentrations over longer periods of time. An important advantage of the present invention is that an implant system for filling bone cavities and for fixing bone fragments in a living body is now provided, which comprises discretely-shaped, porous bodies impregnated with a high concentration of therapeutically-active component, and a coating of biodegradable substance of varying thickness over at least a portion of one of these discretely-shaped, porous bodies, preferably over a number of these discretely-shaped porous bodies, to thus form the requisite implant system. The release of the therapeutically-active component from the implant system, which depends upon the type of biodegradable substance used or upon the thickness of the layer of biodegradable substance, is gradual with the released quantity of therapeutically-active component from each impregnated discretely-shaped, porous body remaining substantially constant over a period of time.

With uncoated implants, the antiseptic or therapeutically-active substance impregnated within the porous body will be completely released from the ceramic implant within approximately two days. However, this particular period of time is totally inadequate for preventing post-operative infections from occurring when an implant or implant system is inserted for filling bone cavities or for fixing bone fragments within a living body. However, with the implant system provided by the present invention and described herein, control of the initial release of therapeutically-active component from the implant bodies can be facilitated, while the overall time interval of release of therapeutically-active ingredient can be considerably targeted over time, and even extended over a certain period of time to enhance delivery of therapeutic action long after bone implantation, i.e. during the important phase of bone growth or bone healing that occurs after implantation.

This initial release of therapeutically-active ingredient along with the subsequent, extended release of therapeutic ingredient from the implant bodies over a set period of time, can be controlled by selecting and combining the discretely-shaped porous bodies impregnated with therapeutically-active ingredient, in a particular manner so that some of the porous bodies are coated with discrete layers of biodegradable substance of varying thicknesses, while if necessary, certain such porous bodies remain uncoated, so that the danger of infection occurring is correspondingly reduced since the release of therapeutically-active ingredient from the impregnated porous bodies can be precisely controlled from the point of initial implantation. For example, such discretely shaped, porous bodies provided with varying initial release periods of therapeutically-active ingredient impregnated therein (i.e. porous bodies having different thicknesses of biodegradable coating) can be so distributed within a bone cavity that areas more prone to occurring infections can be provided more extensively with therapeutically-active ingredient. Each situation of implantation will naturally depend on the extent to which each, individual porous body is impregnated with therapeutically-active ingredient, and the thickness of the biodegradable substance coating about each such porous body, along with whether or not such porous body is initially coated to begin with.

The present invention will now be described in more detail with reference to exemplary embodiments thereof, which are not intended to limit the scope of the present invention in any way.

DETAILED DESCRIPTION OF PREFERRED EMBODIMENTS

A sintered tricalcium phosphate implant for filling bone cavities and for fixing bone fragments in the living body, comprises a discretely shaped, porous body of tricalcium phosphate, and at least one therapeutically-active ingredient impregnated into this body and distributed among the pores therein. The porous body itself is formed by mixing tricalcium phosphate with at least one substance which under heat sufficiently high to bake the tricalcium phosphate, forms a gas, followed by shaping of the thus-formed mixture into shaped bodies thereof. Such a gas-forming substance may be selected from the group consisting of hydrogen peroxide, urea, sugar, ammonium bicarbonate, ammonium carbamate, calcium hydrogen phosphate, and mixtures thereof. The gas-forming substance which is used, preferably brings about macroporosity and microporosity of the tricalcium phosphate ceramic before and during the baking process, but which at the same time decomposes in residue-free manner in the bone cement. Thus the gas-generating substance may comprise an organic or inorganic substance which is converted into gas such as $NH_3$, $CO_2$, and $H_2O$ during the baking process, so that pore formation takes place upon escape of the gas so formed. Another suitable gas-forming substance which may be included for pore formation is hartshorn salt, which is formed from ammonium bicarbonate and ammonium carbamate, ammonium carbonate, calcium hydrogen phosphate, along with other ingredients.

From about 3% to about 30% by weight of the gas-forming substance, based on the weight of the tricalcium phosphate, is mixed therewith. Preferably, about 10% to about 20% by weight of the gasforming substance, based on the weight of the tricalcium phosphate, is mixed therewith. Concerning specifically-preferred gas-forming agents, the tricalcium phosphate may be mixed with from about 1% to about 3% by weight of hydrogen peroxide, based on the weight of the tricalcium phosphate. The tricalcium phosphate may also be mixed with about 10% to about 20% by weight of urea, based on the weight of the tricalcium phosphate. These two gas-forming substances provide for particular optimization of pore formation within the discretely-shaped porous body that is baked. The pore-forming property of hydrogen peroxide is noted in the above-cited Philips Technische Rundschau publication.

The discretely-shaped, porous body of tricalcium phosphate that has been baked and molded is impregnated with at least one therapeutically-active ingredient which is distributed among the pores within this body. The therapeutically-active ingredient may constitute an antiseptic, a microbicidal, or a chemotherapeutic agent, or a combination of any of these agents. The therapeutically-active ingredient is preferably selected from at least one polyvinyl pyrrolidone iodine, penicillin, cycloserin, bacitracin, nystatin, amphotericin, gentamycin, novobiocin, erythromycin, momycin, streptomycin, flucloxacillin, and sulfonamide. Each individual discretely-shaped, porous body may be impregnated with up to about 45% by weight of the therapeutically-active ingredient based upon the weight of the baked porous body.

In the implant system of the present invention, at least a portion of one of the discretely-shaped, porous bodies is coated with a layer of biodegradable substance having a finite thickness. The biodegradable substance may be a biodegradable polymer, such as a polymer selected from at least one of polylactide and polydextran. Examples of other biodegradable substances which may be used for the coating of the individual porous bodies include, but are not limited to, polymers such as methacrylates, cellulose-base substances, or any other biodegradable coatings and other known dissolvable coatings.

Each discretely-shaped porous body is coated with a biode-gradable substance having a particular thickness, in order to obtain delayed release of the therapeutically-active ingredient impregnated within the porous body. In order to obtain different release times, the coating of biodegradable substance is applied in different, accurately-defined coating thicknesses on the various porous bodies that make up an implant system of the present invention. In the present invention, at least a portion of one such discretely shaped, porous bodies is coated with a finite thickness of biodegradable substance. However, in preferred embodiments of the present invention, several groups of such discretely-shaped, porous bodies are coated with layers of the biodegradable substance of varying thicknesses, with each such group being coated with a particular thickness of such biodegradable substance coating. The thickness of the biodegradable substance coating applied to the porous bodies in each particular group, may be identical to one or more of the thicknesses of the biodegradable substance coating applied to any of the other groups of discretely-shaped, porous bodies. However, it is preferable that the particular thickness of biodegradable substance coating applied to the discretely-shaped porous bodies in each particular group of the implant system of the present invention, is different from any of the other thicknesses of the biodegradable substance coating applied to the porous bodies in any of the other groups, so that a well-controlled, sustained release of therapeutically-active ingredient impregnated within the various porous bodies can be attained over a certain period of time. The speed with which such impregnated therapeutically-active ingredient will be released from each individual porous body, will naturally be determined by the amount of thickness of the biodegradable substance coating about the individual porous body. Therefore, by varying the thicknesses of the biodegradable substance coating over these various groups of porous bodies, such sustained, release of the therapeutically active ingredient from the various porous bodies can be quite precisely controlled and determined to effect desired release at specific time intervals. Additionally, by providing a certain group of such porous bodies with a relatively thin coating of biodegradable substance, or even providing one or more such groups without any coating of biodegradable substance upon the porous bodies of that group, rapid release of such therapeutically active ingredient can be targeted for particular locations where such rapid release is desired within a bone cavity, for example locations of the cavity where the bone might be extremely susceptible to infection. Thus it is possible with the present invention to not only control the time release of therapeutically-active ingredient from the implant system, but to also specifically pinpoint desired location where rapid release of such therapeutically-active ingredient and/or sustained release thereof is also especially desired. Impregnation of the individual porous bodies with differing amounts of therapeutically-active ingredient, together with varying the thickness of biodegradable substance coating as noted above, can also be used to control the overall concentration of therapeutically-active ingredient that is available for release at particular locations within a bone cavity, thus control the overall therapeutic activity that is available at such locations.

The thickness of the biodegradable substance coating about each individual discretely-shaped, porous body may naturally vary as required in accordance with the present invention. Such thickness of the biodegradable substance coating is preferably from about 4 microns to about 30 microns, and more preferably from about 8 microns to about 20 microns. For example, in the implant system of the present invention, one such group of discretely-shaped, porous bodies may be coated with a layer of biodegradable polymer having a thickness of about 8 microns, while a second such group of discretely-shaped, porous bodies may be coated with a layer of biodegradable polymer having a thickness of about 20 microns, and a third such group of discretely-shaped, porous bodies may remain uncoated, to provide for quick action and release of therapeutically-active ingredient from the third such group, followed by slower release of the therapeutically-active ingredient from the first such group, and the slowest, sustained release of therapeutically-active ingredient from the second such group having the thickest coating of biodegradable polymer about the individual porous bodies.

Prior to the baking process, a fluoride component may be preferably added to the tricalcium phosphate to foster better acceptance or resorption of the tricalcium phosphate ceramic by bone tissue, in addition to stimulating growth of new bone structure. The fluoride component is preferably a fluoride compound selected from at least one of alkali metal fluorides and alkaline earth fluorides, and is preferably selected from the group consisting of $CaF_2$, $NaF$, $MgF_2$, and mixtures thereof. Fluoride compounds with elements already occurring in bone tissue may also be utilized. The fluoride adjuvant interrupts the crystalline structure of the tricalcium phosphate matrix, so that quick resorption of the implant through bone tissue is enhanced, along with stimulating regeneration of bone tissue itself.

In the process of producing the sintered tricalcium phosphate implant according to the present invention, tricalcium phosphate is initially mixed with the gas-forming substance. This can be accomplished, for example, by granulating tricalcium phosphate together with the gas-forming substance. It is also possible to shape the tricalcium phosphate together with the gas-forming substance using a slip casting process. The fluoride adjuvant is optionally incorporated into the mixture of tricalcium phosphate and gas-forming substance at this point.

The mixture of tricalcium phosphate and gas-forming substance is then formed into at least one discretely-shaped body, which is then baked or sintered at a temperature sufficiently high to cause gas formation from the gas-forming substance, thereby forming pores within the shaped body itself. The shaped body is preferably baked at a temperature up to about 1000° C., preferably at a temperature up to about 1150° C. It is also possible to use higher or lower temperatures for sintering, as will be readily apparent to one of skill in the art.

After baking has been completed, the shaped, porous body is then impregnated with the therapeutically active ingredient to distribute the same throughout the pores formed within the porous body. Impregnation of polyvinyl pyrrolidone, is advantageously carried out for example, by using a polyvinylpyrrolidone iodine solution or complex as the therapeutically-active component, with a 10% available iodine content (e.g., 1 gram of the polyvinyl pyrrolidone iodine solution or complex contains 10% of available iodine). Such a solution or complex of polyvinyl pyrrolidone iodine has high microbicidal activity, which is especially effective. It is also possible to apply polyvinyl pyrrolidone iodine having varied molecular weight. Impregnation may occur by contacting the shaped, porous bodies with the solution or complex of active ingredient, to allow the same to impregnate into the shaped porous bodies and become distributed throughout the pores therein.

Then, the layer of biodegradable substance is coated onto at least a portion of one of the discretely-shaped, porous bodies that have been impregnated with therapeutically-active ingredient. All of the discretely-shaped, porous bodies so formed may be coated with the biodegradable substance, or only a portion of the discretely-shaped, porous body so formed need be coated, with the rest of the porous bodies remaining uncoated. Additionally, layers of different thicknesses of biodegradable substance may be coated on each individual porous body so formed. One such layer of biodegradable substance of precisely-defined thickness may be coated on an individual porous body, or several discrete layers of the biodegradable substance may be coated, one at a time, about a discretely-shaped, porous body. If it is desired, one or more of such discrete layers of biodegradable substance may be impregnated with therapeutically-active ingredient, to enhance quick release of the same, along with rapid delivery of such therapeutic action.

The following examples further illustrate specific embodiments of the present invention, which is not limited in scope by any of the following examples.

EXAMPLE 1

Commercial tricalcium phosphate having a particle size of approximately 1 to 2 microns, is granulated on a pan granulator by adding water, and is then mixed with hydrogen peroxide, i.e. the gas-forming substance, in an amount of about 3% by weight of the tricalcium phosphate with which the hydrogen peroxide is mixed. If it is desired, calcium fluoride may be added as a suitable resorption accelerator.

The granules obtained by mixing are sufficiently stable to be separated into fractions of different sizes using screens. The finished granulate is then baked for about 1 hour at a temperature of about 1150° C. (the baking temperature may be varied higher or lower as required). The granulates obtained have adequate mechanical strength and are able to absorb adequate quantities of a therapeutically-active ingredient, such as a disinfectant, antiseptic agent, chemotherapeutic agent or broad-spectrum microbicide such as a polyvinyl pyrrolidone iodine solution or complex.

The baked granulate is then impregnated with a polyvinyl pyrrolidone iodine solution or complex in which one gram contains 10% of available iodine, and is subsequently dried. The granulate absorbes the dry therapeutically-active ingredient at a content of up to about 45% of the ceramic starting weight. After the granulate has dried after being impregnated with therapeutically-active ingredient, the granules are divided into individual groups with each group then being coated with a layer of biodegradable substance, in this case polymethacrylate, having a particular thickness. The thickness of the polymethacrylate layer applied to one group of these granules is about 8 microns, while the thickness of the polymethacrylate layer applied to the second group of granules is about 20 microns. Additionally, one group of the granules remains uncoated.

Gas-forming agent which may be used instead of, or in addition to hydrogen peroxide, includes urea, sugar, ammonium bicarbonate, ammonium carbamate, calcium hydrogen phosphate, hartshorn salt, and mixtures of any of these ingredients. Therapeutically active ingredient which may be used instead of, or in addition to the polyvinyl pyrrolidone iodine includes penicillin, cycloserin, bacitracin, nystatin, amphotericin, gentamycin, novobiocin, erythromycin, momycin, streptomycin, flucloxacillin, sulfonamide, and mixtures of any of these. Fluoride adjuvant which may be used instead of or in addition to calcium fluoride, includes sodium fluoride, magnesium fluoride, and mixtures of these. Biodegradable polymer which may be used as the coating instead of or in addition to polymethacrylate, includes polylactide, polydextran, and mixtures of these.

EXAMPLE 2

Commercial tricalcium phosphate having a particle size of about 1 to 2 microns, is granulated using a fluid-bed spray granulation technique known in the pharmaceutical art, by adding a suitable granulating liquid. 20% by weight of ammonium bicarbonate as the gas-generating substance, calcium fluoride as the resorption-enhancing adjuvant, are added to the tricalcium phosphate during granulating (weight percent are based on the weight of the tricalcium phosphate).

The dry granulate mixture that is obtained is then pressed into tablet blanks on a suitable tableting machine. The finished tablets are then baked for approximately 1 hour at a temperature of about 1150° C., although higher or lower temperatures can also be used for baking depending upon the desired mechanical strength of the tablets. The baked tablets are able to absorb adequate quantities of the therapeutically-active ingredient, such as a disinfectant, antiseptic agent, chemotherapeutic agent, or a broad-spectrum microbicide such as a polyvinyl pyrrolidone-iodine solution or complex.

The individual tablets are then impregnated with a solution of polyvinyl pyrrolidone iodine, where one gram of this solution has a 10% content of available iodine, and the tablets are subsequently dried. The tablets absorb a dry content of the therapeutically-active ingredient of up to about 45% by weight of the initial ceramic weight.

The dry tablets are then divided into groups, and each group is coated with at least one layer of polydextran having a discrete thickness, to control the release of the therapeutically active ingredient from the individual tablets. One such group of tablets has a coating of polydextran about 8 microns thick, a second group of such tablets has a coating of polydextran about 20 microns thick, while optionally, a third group of such tablets may remain uncoated.

Other suitable gas-forming agents which may be used instead of, or in addition to the ammonium bicarbonate, include hydrogen peroxide, urea, sugar, ammonium carbamate, calcium hydrogen phosphate, hartshorn salt, and mixtures of these. Fluoride adjuvant which may be used instead of or in addition to calcium fluoride, includes sodium fluoride, magnesium fluoride, and mixtures of these. Therapeutically-active ingredient which may be used instead of or in addition to polyvinyl pyrrolidone iodine includes penicillin, cycloserin, bacitracin, nystatin, amphotericin, gentamycin, novobiocin, erythromycin, momycin, streptomycin, flucloxacillin, sulfonamide, and mixtures of any of these. Other biodegradable polymer which may be coated on the tablets instead of or in addition to polydextran includes polymethacrylate, polylactide, and mixtures of these.

EXAMPLE 3

Commercial tricalcium phosphate having a particle size of about 1 to 2 microns, along with about 20% by weight of ammonium carbamate and calcium fluoride (the percents are based on the weight of tricalcium phosphate) are all mixed together and formed into a paste by adding a suitable liquid such as water. The resulting mixture is then placed into molds of any appropriate random size, followed by baking for about 1 hour at a temperature of about 1150° C. (a lower or higher temperature may be used depending upon the desired strength of the blanks that are molded). The porous blanks so obtained are able to absorb adequate quantities of a therapeutically-active ingredient such as a disinfectant, antiseptic agent, chemotherapeutic agent, or microbicide.

The shaped blanks that have been baked are impregnated with a polyvinyl pyrrolidone iodine complex or solution, in which one gram contains approximately 10% of available iodine. The blanks are able to absorb a dry therapeutically-active ingredient content of up to about 45% of the initial ceramic weight.

The baked and shaped porous blanks that have been impregnated with therapeutically-active ingredient, are then all divided up into several groups, with each group being coated with appropriate biode-gradable substance in the same manner as the granulate in Example 1 is coated, or in the same manner as the tablets in Example 2 are coated. In other words, the molded blanks are divided into several groups, with the blanks in the first group being coated with polymethacrylate having a thickness of about 8 microns, the second group of blanks being coated with polymethacrylate having a thickness of about 20 microns, the third such group of blanks being coated with polydextran having a thickness of about 8 microns, the fourth such group of blanks being coated with polydextran having a thickness of about 20 microns, while a fifth such group of these molded, porous, and impregnated blanks remains uncoated.

Hydrogen peroxide, urea, sugar, ammonium bicarbonate, calcium hydrogen phosphate, hartshorn salts, and mixtures of these, may be used instead of or in addition to the ammonium carbamate. Sodium fluoride and magnesium fluoride or mixtures of these may be used instead of or in addition to the calcium fluoride. Therapeutically active ingredients which may be used instead of, or in addition to the polyvinyl pyrrolidone iodine includes penicillin, cycloserin, bacitracin, nystatin, amphotericin, gentamycin, novobiocin, erythromycin, momycin, streptomycin, flucloxacillin, sulfonamide, and mixtures of any of these. Polylactide may be used instead of, or in addition to the polymethacrylate and the polydextran serving as the coating of biodegradable polymer.

EXAMPLE 4

A group of porous granules is prepared, impregnated, and coated in accordance with the present invention as set forth in Example 1, with the granules being divided into at least three groups, and being coated with discrete layers of polylactide. The first such group of granules is coated with a thickness of polylactide about 8 microns, while the second such group of granules is coated with polylactide having a thickness of about 20 microns. The third such group of these granules remains uncoated.

Tablets are prepared, baked, impregnated, and coated in the same manner as the tablets prepared in Example 2, with the tablets also being coated with polylactide and divided into discrete groups depending on the thickness of the coating thereof. The first such group of these tablets are also coated with polylactide having a thickness of about 8 microns, the second such group with polylactide having a thickness of about 20 microns, while the third such group of tables remains uncoated.

Porous blanks are prepared, baked, impregnated with therapeutically-active ingredient, and divided into groups and coated in a similar manner to the blanks that are prepared in Example 3, with these blanks also being coated with polylactide and being divided into at least three discrete groups, the first such group being coated with polylactide having a thickness of about 8 microns, the second such group of blanks being coated with polylactide of a thickness of about 20 microns, while the third such group remains uncoated.

The groups of granules, and/or tablets, and/or molded blanks prepared in this manner constitute an implant system in accordance with the present invention for filling bone cavities and for fixing bone fragments in a living body. In each of these implant systems, the particular thicknesses of the layers of biodegradable polymer, i.e. polylactide, has been chosen to precisely control the release of therapeutically-active ingredient from within the requisite implant system, i.e. control the delivery of therapeutic action. The thickness of 8 microns of polylactide coating is chosen to specifically delay release of therapeutically-active ingredient from the appropriately-coated bodies to about two weeks after implantation in bone. The polylactide coating thickness of about 20 microns is designed to delay release of therapeutically-active ingredient from the appropriately-coated porous bodies for about four weeks after implantation. The groups of porous bodies that are not coated with any biodegradable polymer will naturally begin to release therapeutically-active ingredient more or less immediately upon implantation.

Thus by discretely selecting the thickness of biodegradable polymer coating about a porous body in such a group within the implant system of the present invention, it is now possible to precisely control and determine the time for release of therapeutically-active ingredient impregnated within the respectively coated porous bodies within such an implant system. Granules, tablets, and blanks prepared and coated in accordance with the present invention, may all be combined together in any requisite proportion to form an implant system in accordance with the present invention. Such an implant system, which is composed of any possible combinations of granules, tablets, and blanks as prepared in accordance with Examples 1-3, or in accordance with the present Example, also results in precise, controlled release of therapeutically-active ingredient from the individual bodies constituting the system, as determined by the particular coating of biodegradable polymer upon such porous bodies. Additionally, shaped, porous bodies of different dimensions but all having a coating of biodegradable polymer of substantially the same thickness, may be prepared in accordance with the present invention, to form a requisite implant system. Polymethacrylate, polydextran, and mixtures of these may be used in place of, or in addition to polylactide coating as the biodegradable polymer.

The preceding description of the present invention is merely exemplary, and is not intended to limit the scope thereof in any way.

What is claimed is:

1. Method of producing sintered tricalcium phosphate implants for filling bone cavities and for fixing bone fragments in a living body, which comprises
   mixing tricalcium phosphate with at least one substance which under heat sufficiently high to bake said tricalcium phosphate, forms a gas,
   shaping the thus-formed mixture into shaped bodies thereof,
   baking the shaped bodies at a temperature sufficiently high to cause gas formation from said substance, thereby forming pores in said shaped bodies,
   impregnating said shaped porous bodies with a therapeutically-active ingredient, thereby distributing the same in the pores, and
   coating at least a portion of one of said shaped, porous bodies having said therapeutically-active ingredient distributed therein, with a coating of a predetermined thickness of a biodegradable substance,
   whereby the time of absorption of said therapeutically-active ingredient is controlled by the thickness of said biodegradable substance.

2. The method of claim 1 in which said gas-forming substance is selected from a group consisting of hydrogen peroxide, urea, sugar, ammonium bicarbonate, ammonium carbamate, calcium hydrogen phosphate, and mixtures thereof.

3. The method of claim 2 in which about 1% to about 3% by weight of hydrogen peroxide, based on the weight of said tricalcium phosphate, is mixed therewith.

4. The method of claim 2 in which about 10% to about 20% by weight of urea, based on the weight of said tricalcium phosphate, is mixed therewith.

5. The method of claim 1 in which about 3% to about 30% by weight of said gas-forming substance, based on the weight of said tricalcium phosphate, is mixed therewith.

6. The method of claim 5 in which about 10% to about 20% by weight of said gas-forming substance, based on the weight of said tricalcium phosphate, is mixed therewith.

7. The method of claim 1 in which said shaped, porous bodies are impregnated with up to about 45% by weight of said therapeutically-active ingredient, based upon the weight of said baked, porous bodies.

8. The method of claim 7 in which said therapeutically-active ingredient is selected from the group consisting of polyvinyl pyrrolidone iodine, penicillin, cycloserin, bacitracin, nystatin, amphotericin, gentamycin, novobiocin, erythromycin, momycin, streptomycin, flucloxacillin, sulfonamide and mixtures thereof.

9. The method of claim 7 in which said therapeutically-active ingredient is polyvinyl pyrrolidone iodine.

10. The method of claim 9 in which said shaped, porous bodies are impregnated with a solution or complex of polyvinyl pyrrolidone iodine having about a 10% iodine content.

11. The method of claim 1 in which said biodegradable substance is selected from at least one of polymethacrylate, polylactide, and polydextran.

12. The method of claim 1 comprising the additional step of mixing at least one fluoride compound selected from at least one of alkaline metal fluorides and alkali earth fluorides, with said tricalcium phosphate prior to baking.

13. The method of claim 12 in which said fluoride compound is selected from the group consisting of $CaF_2$, $NaF$, $MgF_2$, and mixtures thereof.

14. The method of claim 1 in which the thus-formed mixture is formed into a plurality of bodies each having its own discrete shape and dimensions, which are subsequently baked to form said discretely-shaped, porous bodies.

15. The method of claim 1 wherein said biodegradable substance is coated to have a predetermined thickness from about 4 microns to about 30 microns on said porous bodies.

16. The method of claim 15 wherein said bidegradable substance is coated to have a predetermined thickness of about 8 microns to about 20 microns on said porous bodies.

17. A sintered tricalcium phosphate implant for filling bone cavities and for fixing bone fragments in a living body, comprising
 a discretely-shaped, baked porous body of tricalcium phosphate,
 at least one therapeutically-active ingredient impregnated into said porous body and distributed among the pores therein, and
 at least one coating of predetermined thickness of a biodegradable substance on at least a portion of said porous body impregnated with said therapeutically-active ingredient,
 whereby the time of absorption of said therapeutically-active ingredient is controlled by the thickness of said biodegradable substance.

18. The implant of claim 17 wherein said discretely-shaped porous body of tricalcium phosphate, is formed by
 mixing the same with at least one substance which under heat sufficiently high to bake said tricalcium phosphate, forms a gas; and
 baking said shaped body at a temperature sufficiently high to cause gas formation from said substance, thereby forming a discretely-shaped, porous body of tricalcium phosphate.

19. The implant of claim 18, wherein said gas-forming substance is selected from the group consisting of hydrogen peroxide, urea, sugar, ammonium bicarbonate, ammonium carbamate, calcium hydrogen phosphate, and mixtures thereof.

20. The implant of claim 19 wherein about 1% to about 3% by weight of hydrogen peroxide, based on the weight of said tricalcium phosphate, is mixed therewith.

21. The implant of claim 19 wherein about 10% to about 20% by weight of urea, based on the weight of said tricalcium phosphate, is mixed therewith.

22. The implant of claim 17, in which said therapeutically-active ingredient is selected from the group consisting of polyvinyl pyrrolidone iodine, penicillin, cycloserin, bacitracin, nystatin, amphotericin, gentamycin, novobiocin, erythromycin, momycin, streptomycin, flucloxacillin, sulfonamide and mixtures thereof.

23. The implant of claim 17, in which said biodegradable substance is selected from at least one of polymethacrylate, polylactide, and polydextran.

24. The implant of claim 22, in which said shape, porous body is impregnated with up to about 45% by weight of said therapeutically-active ingredient, based upon the weight of said baked, porous body.

25. The implant of claim 24, wherein said therapeutically-active ingredient is polyvinyl pyrrolidone iodine.

26. The implant of claim 17, in which said discretely-shaped, porous body of tricalcium phosphate additonally comprises at least one fluoride compound selected from at least one of alkali metal fluorides and alkaline earth fluorides.

27. The implant of claim 26, in which said fluoride compound is selected from the group consisting of $CaF_2$, $NaF$, $MgF_2$, and mixtures thereof.

28. The implant of claim 17 wherein the thickness of said biodegradable substance is from about 4 microns to about 30 microns.

29. The implant of claim 28 wherein the thickness of said biodegradable substance is from about 8 microns to about 20 microns.

30. A sintered tricalcium phosphate implant for filling bone cavities and for fixing bone fragments in a living body, prepared by the method according to claim 1.

31. An implant system for filling bone cavities and for fixing bone fragments in a living body, said system comprising
 discretely-shaped, porous bodies of tricalcium phosphate,
 at least one therapeutically-active ingredient impregnated into said porous bodies and distributed among the pores therein, and
 at least one coating of predetermined thickness of a biodegradable substance on at least a portion of one of said porous bodies impregnated with said therapeutically-active ingredient,
 whereby the time of absorption of said therapeutically-active ingredient is controlled by the thickness of said biodegradable substance.

32. The system of claim 31 wherein at least one porous body is coated with said biodegradable substance having a thickness of about 8 microns, at least one other porous body is coated with biodegradable substance having a thickness of about 20 microns, and at least a third porous body remains uncoated.

33. A method for filling bone cavities and for fixing bone fragments after fractures, which comprises employing an implant system according to claim 31.

* * * * *